United States Patent
Kaji et al.

(10) Patent No.: US 6,903,180 B2
(45) Date of Patent: Jun. 7, 2005

(54) EPOXY RESINS, PROCESS FOR PREPARATION THEREOF, EPOXY RESIN COMPOSITIONS AND CURED ARTICLES

(75) Inventors: Masashi Kaji, Tokyo (JP); Koichiro Ogami, Fukuoka (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 174 days.

(21) Appl. No.: 10/433,365

(22) PCT Filed: Dec. 10, 2001

(86) PCT No.: PCT/JP01/10798

§ 371 (c)(1),
(2), (4) Date: Jun. 4, 2003

(87) PCT Pub. No.: WO02/48235

PCT Pub. Date: Jun. 20, 2002

(65) Prior Publication Data

US 2004/0024167 A1 Feb. 5, 2004

(30) Foreign Application Priority Data

Dec. 11, 2000 (JP) .......................................... 2000-376351

(51) Int. Cl.⁷ .......................... C08G 59/00; C08G 73/00; C08L 63/00
(52) U.S. Cl. ............................. 528/96; 528/87; 528/98; 528/99; 528/212; 528/219; 528/367; 528/405; 528/421; 528/423
(58) Field of Search .................. 528/86, 87, 96, 528/98, 99, 106, 116, 118, 119, 212, 219, 367, 403, 405, 421, 422, 423

(56) References Cited

U.S. PATENT DOCUMENTS 3,948,916 A    4/1976   Porret et al.

FOREIGN PATENT DOCUMENTS

| EP | 0355728 A2 | 2/1990 | |
| JP | 62294784 A | 12/1987 | |
| JP | 02-240080 * | 9/1990 | ......... C07D/405/14 |
| JP | 02-279684 | 11/1990 | |
| JP | 03121280 A | 5/1991 | |
| JP | 08-081461 | 3/1996 | |
| JP | 2768426 * | 6/1998 | ......... C07D/405/14 |
| KR | 1988-22049 | 12/1988 | |

OTHER PUBLICATIONS

Derwent Abstract 1990–3352366 (for JP 02–240080 & JP 2768426).*
International Search Report for PCT/JP01/10798 mailed on Mar. 5, 2002.
English translation of International Preliminary Examination Report for PCT/JP01/10798 completed on May 28, 2002.

* cited by examiner

*Primary Examiner*—Michael J. Feely
(74) *Attorney, Agent, or Firm*—Rader, Fishman & Grauer PLLC

(57) ABSTRACT

This invention relates to novel epoxy resins and epoxy resin compositions comprising said epoxy resins or cured articles thereof. The cured articles have excellent properties in respect to flame retardance, adhesiveness, moisture resistance and heat resistance and can be used in applications such as lamination, molding, casting and adhesion. The epoxy resins of this invention are represented by the following formula (3)

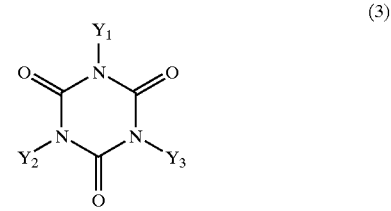

(3)

wherein $Y_1$ denotes a glycidyloxyarylmethyl group represented by —$CH_2$—Ar—OG, $Y_2$ and $Y_3$ denote independently a glycidyl group or the aforementioned glycidyloxyarylmethyl group, Ar denotes a phenylene group which can be substituted with up to two hydrocarbon groups and G denotes a glycidyl group.

4 Claims, 4 Drawing Sheets

EPOXY RESINS, PROCESS FOR PREPARATION THEREOF, EPOXY RESIN COMPOSITIONS AND CURED ARTICLES

FIELD OF TECHNOLOGY

This invention relates to epoxy resins which cure to yield articles with excellent flame retardancy, moisture resistance, heat resistance and adhesiveness to metallic substrates and to compositions of said epoxy resins and cured articles of said compositions. The epoxy resin compositions in question are suited for use as insulating materials for electrical and electronic applications involving printed wiring boards and encapsulation of semiconductors.

BACKGROUND TECHNOLOGY

Keeping pace with the progress of materials for advanced technologies in recent years, there is a growing demand for base resins of increasingly higher performance for such materials. In the area of encapsulation of semiconductors, for example, the packages are becoming smaller in thickness and larger in area and the technique of surface mounting is coming into wider use in response to the trend of higher-density packaging in recent years. As the result, cracking of packages has caused a serious problem and there is a strong demand for availability of base resins with improved properties in respect to moisture resistance, heat resistance and adhesiveness to metallic substrates. From the standpoint of reduction of environmental load, the trend of public opinion is to exclude the use of halogen-containing flame retardants and there is a demand for base resins of improved flame retardance.

However, none of existing epoxy resins is known to satisfy the aforementioned property requirements. For example, universally known bisphenol type epoxy resins are widely used as they are liquid at room temperature, easy to work with and readily mixable with curing agents and additives, but they present problems concerning heat resistance and moisture resistance. Novolak type epoxy resins are known for improved heat resistance, but they still have problems concerning moisture resistance and adhesiveness. Furthermore, the conventional epoxy resins whose backbone is composed of hydrocarbons alone completely lack flame retardance.

As a means to improve flame retardance without the use of halogen-containing flame retardants, addition of flame retardants based on phosphate esters is disclosed in JP09-235449-A, JP10-182792-A and elsewhere. However, the use of flame retardants based on phosphate esters does not provide sufficient moisture resistance. Moreover, phosphate esters undergo hydrolysis in an environment of high temperature and high moisture thereby adversely influencing the reliability as insulating material.

DISCLOSURE OF THE INVENTION

Accordingly, an object of this invention is to provide epoxy resins which have excellent properties in respect to flame retardance, moisture resistance, heat resistance and adhesiveness to metallic substrates and are useful for applications such as lamination, molding, casting and adhesion and, further, to provide epoxy resin compositions comprising said epoxy resins and curing agents and cured articles of said compositions.

The epoxy resins of this invention are represented by the following general formula (3)

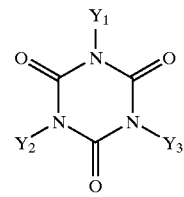

wherein $Y_1$, $Y_2$ and $Y_3$ denote a glycidyl group or a glycidyloxyarylmethyl group represented by the following general formula (4)

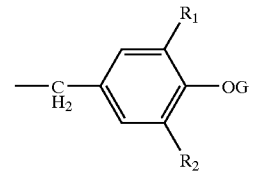

(wherein $R_1$ and $R_2$ denote independently a hydrogen atom or a hydrocarbon group containing 1 to 8 carbon atoms and G is a glycidyl group) and at least one of $Y_1$, $Y_2$ and $Y_3$ is a glycidyloxyarylmethyl group.

The process for preparing the epoxy resins of this invention is based on the reaction of a hydroxy compound represented by the following general formula (1) with epichlorohydrin;

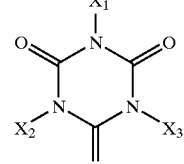

wherein $X_1$, $X_2$ and $X_3$ denote independently a hydrogen atom or a hydroxyarylmethyl group represented by the general formula (2)

(2)

—C(H_2)—⟨aryl⟩—OH with $R_1$, $R_2$ (wherein $R_1$ and $R_2$ denote independently a hydrogen atom or a hydrocarbon group containing 1 to 8 carbon atoms) and at least one of $X_1$, $X_2$ and $X_3$ is a hydroxyarylmethyl group.

The epoxy resin compositions of this invention comprise the aforementioned epoxy resins as essential components.

The cured epoxy resin articles of this invention are the products obtained by curing the aforementioned epoxy resin compositions.

The hydroxy compound to be used as a starting material in the preparation of the epoxy resins of this invention is represented by the general formula (1). In the formula, $X_1$, $X_2$ and $X_3$ denote either a hydrogen atom or a hydroxyarylmethyl group represented by the general formula (2), but there is no case where $X_1$, $X_2$ and $X_3$ are all hydrogen atoms. To be concrete, $X_1$ is a hydroxyarylmethyl group, both $X_1$ and $X_2$ are hydroxyarylmethyl groups, or $X_1$, $X_2$ and $X_3$ are all hydroxyarylmethyl groups. The starting material in the process for preparing the epoxy resins of this invention may be one kind or a mixture of two or three kinds of the aforementioned three kinds of hydroxy compounds. In case a mixture is used, a hydroxy compound in which $X_1$, $X_2$ and $X_3$ are all hydroxyarylmethyl groups preferably accounts for 30 wt % or more of the total hydroxy compounds. There may be a case where the hydroxy compounds contain isocyanuric acid or a hydroxy compound in which $X_1$, $X_2$ and $X_3$ are all hydrogen atoms as impurities and, in such a case, the content of isocyanuric acid is preferably kept below 30 wt %.

In the general formula (2), $R_1$ and $R_2$ are hydrogen atoms or hydrocarbon groups containing 1 to 8 carbon atoms and the hydrocarbon groups include, for example, methyl, ethyl, n-propyl, isopropyl, n-butyl, sec-butyl, tert-butyl, n-amyl, sec-amyl, tert-amyl, cyclohexyl, phenyl and benzyl. However, it is not desirable that $R_1$ and $R_2$ are simultaneously tertiary hydrocarbon groups such as tert-butyl and tert-amyl for the reason that the reactivity in the synthesis of epoxy resins decreases in the case where $R_1$ and $R_2$ cause large steric hindrance. Preferably, one of $R_1$ and $R_2$ is a hydrogen atom or a primary or secondary alkyl group containing 1 to 8 carbon atoms and, more preferably, $R_1$ and $R_2$ are hydrogen or methyl.

The hydroxy compounds are obtained by the reaction of a phenol such as phenol, cresol, 2,6-xylenol and 2-phenylphenol, with cyanuric acid and paraformaldehyde. When the molar ratio of a phenol to cyanuric acid is controlled at 3:1 or at a value higher than 3:1, the reaction preferentially yields a product which is a compound represented by general formula (1) wherein $X_1$, $X_2$ and $X_3$ are all hydroxyarylmethyl groups. When the molar ratio is controlled at a value lower than 3:1, the reaction product is a mixture of three kinds of compounds respectively represented by general formula (1) wherein $X_1$ alone is a hydroxyarylmethyl group, $X_1$ and $X_2$ are hydroxyarylmethyl groups and $X_1$, $X_2$ and $X_3$ are hydroxyarylmethyl groups. These compounds can be separated and purified by a means such as recrystallization and chromatographic separation.

The aforementioned hydroxy compounds are suited for use not only as intermediates for epoxy resins but also as curing agents for epoxy resins. Likewise, those hydroxy compounds which are obtained by the reaction of a naphthol such as 1-naphthol, 2-naphthol and 2-methyl-1-naphthol with cyanuric acid and paraformaldehyde are suited for use not only as intermediates for epoxy resins but also as curing agents for epoxy resins.

An advantageous process for preparing the epoxy resins of this invention is the reaction of a hydroxy compound represented by the general formula (1) with epichlorohydrin, but is not limited to this particular reaction. The aforementioned reaction of a hydroxy compound with epichlorohydrin can be carried out similarly to an ordinary epoxidation reaction.

The process for preparing epoxy resins of this invention is based on the reaction of a hydroxy compound represented by the general formula (1) with epichlorohydrin. The product is epoxy resins represented by the general formula (3) or the product comprises said epoxy resins as principal components. The reaction of the aforementioned hydroxy compound with epichlorohydrin can be carried out similarly to an ordinary epoxidation reaction.

For example, a hydroxy compound represented by the general formula (1) is dissolved in an excess of epichlorohydrin and the reaction is allowed to proceed in the presence of an alkali metal hydroxide such as sodium hydroxide and potassium hydroxide at 50–150° C., preferably at 60–120° C., for 1–10 hours. The amount of alkali metal hydroxide to be used here is 0.8–1.2 moles, preferably 0.9–1.0 mole, per 1 mole of the total of hydroxy and N—H groups in the hydroxy compound. Epichlorohydrin is used in excess of the total amount of hydroxy and N—H groups in the hydroxy compound, normally 1.5–30 moles, preferably 2–15 moles, per 1 mole of the total amount of hydroxy and N—H groups in the hydroxy compound. Upon completion of the reaction, the excess epichlorohydrin is distilled off and the remainder is dissolved in a solvent such as toluene and methyl isobutyl ketone, filtered, washed with water to remove inorganic salts and stripped of the solvent by distillation to give the target epoxy resins.

The epoxy resins of this invention are represented by the general formula (3) and $Y_1$, $Y_2$ and $Y_3$ denote a glycidyl group or a glycidyloxyarylmethyl group represented by the general formula (4) but they are not glycidyl groups simultaneously. To be concrete, the epoxy resins of this invention comprise three kinds of epoxy resins, namely, $Y_1$ is a glycidyloxyarylmethyl group, both $Y_1$ and $Y_2$ are glycidyloxyarylmethyl groups or $Y_1$, $Y_2$ and $Y_3$ are all glycidyloxyarylmethyl groups.

The epoxy resins of this invention may be a mixture of two or three kinds and, in such a case, the epoxy resins in which $Y_1$, $Y_2$ and $Y_3$ are all glycidyloxyarylmethyl groups preferably account for 20 wt % or more of the total. There may be an instance where the epoxy resins of this invention contain triglycidylisocyanuric acid or the compound in which $Y_1$, $Y_2$ and $Y_3$ are all glycidyl groups as impurities and, in that case, the content of triglycidylisocyanuric acid is preferably kept below 30 wt %. The epoxy resins of this invention comprise a compound or a mixture of compounds represented by the general formula (3) and they may further contain partial polymers of the compound or mixture in question.

The epoxy resins in which $Y_1$, $Y_2$ and $Y_3$ are all glycidyloxyarylmethyl groups can be obtained readily from the hydroxy compounds in which $X_1$, $X_2$ and $X_3$ are all hydroxyarylmethyl groups. Likewise, the epoxy resins in which one or two of $Y_1$, $Y_2$ and $Y_3$ are glycidyloxyarylmethyl groups can be obtained readily from the corresponding hydroxy compounds.

The epoxy resins of this invention and formulated together with curing agents into compositions and used in a variety of applications.

In the general formula (4), $R_1$ and $R_2$ are hydrogen atoms or hydrocarbon groups containing 1 to 8 carbon atoms and examples of $R_1$ and $R_2$ here are similar to those cited for $R_1$ and $R_2$ in the general formula (2). Moreover, it is not desirable that $R_1$ and $R_2$ are simultaneously tertiary hydrocarbon groups such as tert-butyl and tert-amyl. This is because the reactivity in curing as epoxy resins decreases when $R_1$ and $R_2$ cause large steric hindrance. Hydrogen or methyl is preferably selected for $R_1$ and $R_2$.

The epoxy resin compositions of this invention contain epoxy resins and curing agents and comprise the epoxy resins represented by the general formula (3) as essential components.

Curing agents to be incorporated in the aforementioned epoxy resin compositions may be any of curing agents generally known for epoxy resins, for example, dicyandiamide, polyhydric phenols, acid anhydrides and aromatic and aliphatic amines.

Concrete examples are dihydric phenols such as bisphenol A, bisphenol F, bisphenol S, fluorenebisphenol, 4,4'- biphenol, 2,2'-biphenol, hydroquinone, resorcin and naphthalenediol and trihydric and higher phenols such as tris(4-hydroxyphenyl)methane, 1,1,2,2-tetrakis(4-hydroxyphenyl) ethane, phenol novolak, o-cresol novolak, naphthol novolak and polyviylphenol. Further, examples include polyhydric phenols synthesized from monohydric phenols and naphthols or dihydric phenols such as bisphenol A, bisphenol F, bisphenol S, fluorenebisphenol, 4,4'-biphenol, 2,2'-biphenol, hydroquinone, resorcin and naphthalenediol and condensing agents such as formaldehyde, acetaldehyde, benzaldehyde, p-hydroxybenzaldehyde and p-xylylene glycol. Still further, examples include the hydroxy compounds represented by the general formula (1) wherein $R_1$ and $R_2$ are preferably hydrogen or methyl.

Acid anhydrides useful as curing agents include phthalic anhydride, tetrahydrophthalic anhydride, methyltetrahydrophthalic anhydride, hexahydrophthalic anhydride, methylhexahydrophthalic anhydride, methylhimic anhydride, nadic anhydride and trimellitic anhydride.

Amines useful as curing agents include aromatic amines such as 4,4'-diaminodiphenylmethane, 4,4'-diaminodiphenylpropane, 4,4-diaminodiphenyl sulfone, m-phenylenediamine and p-xylylenediamine and aliphatic amines such as ethylenediamine, hexametnylenediamine, diethylenetriamine and triethylenetetramine.

The resin compositions of this invention may contain one kind or a mixture of two kinds or more of the aforementioned curing agents. It is advantageous to use the hydroxy compounds represented by the general formula (1) as a part of the curing agents and, in that case, the amount of the hydroxy compounds in question is 5–100%, preferably 60–100%, of the total hydroxy compounds or curing agents.

Epoxy resins other than the epoxy resins of this invention may be used as epoxy resin component in formulating the epoxy resin compositions of this invention. In such a case, ordinary epoxy resins containing two or more epoxy groups in the molecule may be used as other epoxy resins; for example, glycidyl ethers derived from dihydric phenols such as bisphenol A, bisphenol F, 3,3', 5,5'-tetramethylbisphenol F, bisphenol S, fluorenebisphenol, 4,4'-biphenol, 3,3,5,5'-tetramethyl-4,4'-biphenol, 2,2'-biphenol, hydroquinone and resorcin, glycidyl ethers derived from trihydric or higher phenols such as tris(4-hydroxyphenyl)methane, 1,1,2,2-tetrakis(4-hydroxyphenyl)ethane, phenol novolak and o-cresol novolak and glycidyl ethers derived from halogenated bisphenols such as tetrabromobisphenol A. These epoxy resins may be used singly or as a mixture of two kinds or more. The amount of the epoxy resins represented by general formula (3) to be incorporated in the epoxy resin compositions of this invention is 5–100%, preferably 60–100%, of the total epoxy resins.

It is allowable to incorporate in the epoxy resin compositions of this invention oligomers or high-molecular-weight compounds such as polyesters, polyamides, polyimides, polyethers, polyurethanes, petroleum resins, indene-coumarone resins and phenoxy resins or additives such as inorganic fillers, pigments, flame retardants, thixotropic agents, coupling agents and flow modifiers. The inorganic fillers include silica powder such as spherical or pulverized molten silica and crystalline silica, alumina powder, glass powder, mica, talc, calcium carbonate, alumina and hydrated alumina. The pigments include organic or inorganic extender pigments and scaly pigments. The thixotropic agents include those based on silicone and castor oil, aliphatic amide waxes, polyethylene oxide waxes and organic bentonites. Furthermore, as occasion demands, the resin compositions of this invention may contain parting agents such as carnauba wax and OP wax, coupling agents such as γ-glycidoxypropyltrimethoxysilane, pigments such as carbon black, flame retardants such as antimony trioxide, stress-relaxing agents such as silicone oils and lubricants such as calcium stearate.

Still more, it is allowable to incorporate known curing accelerators in the resin compositions of this invention as occasion demands; for example, amines, imidazoles, phosphines and Lewis acids. The amount of such curing accelerators is normally 0.2–5 parts by weight per 100 parts by weight of epoxy resins.

The cured artilces of the resin compositions of this invention can be obtained by molding the aforementioned epoxy resin compositions by a technique such as casting, compression molding and transfer molding normally at a temperature in the range of 120–220° C.

PREFERRED EMBODIMENTS OF THE INVENTION

This invention will be described concretely with reference to the accompanying examples and comparative examples.

SYNTHESIS EXAMPLE 1

Synthesis of Hydroxy Compound

In a 2-L four-necked flask were placed 201.3 g of 2,6-xylenol, 67.7 g of cyanuric acid, 62.0 g of 92% paraformaldehyde, 1.76 g of hexamethylenetetramine, 584 g of dimethylformamide and 15.75 g of pure water and the mixture was allowed to react under reflux at approximately 116° C. for 40 hours in a stream of nitrogen. After the reaction was over, the reaction mixture was cooled with stirring to approximately 5° C. to precipitate crystals and the crystals were filtered, washed with methanol and dried under reduced pressure to give 235 g of a hydroxy compound in white powder. The melting point of the compound was 247–248.3° C.

Figure 1:
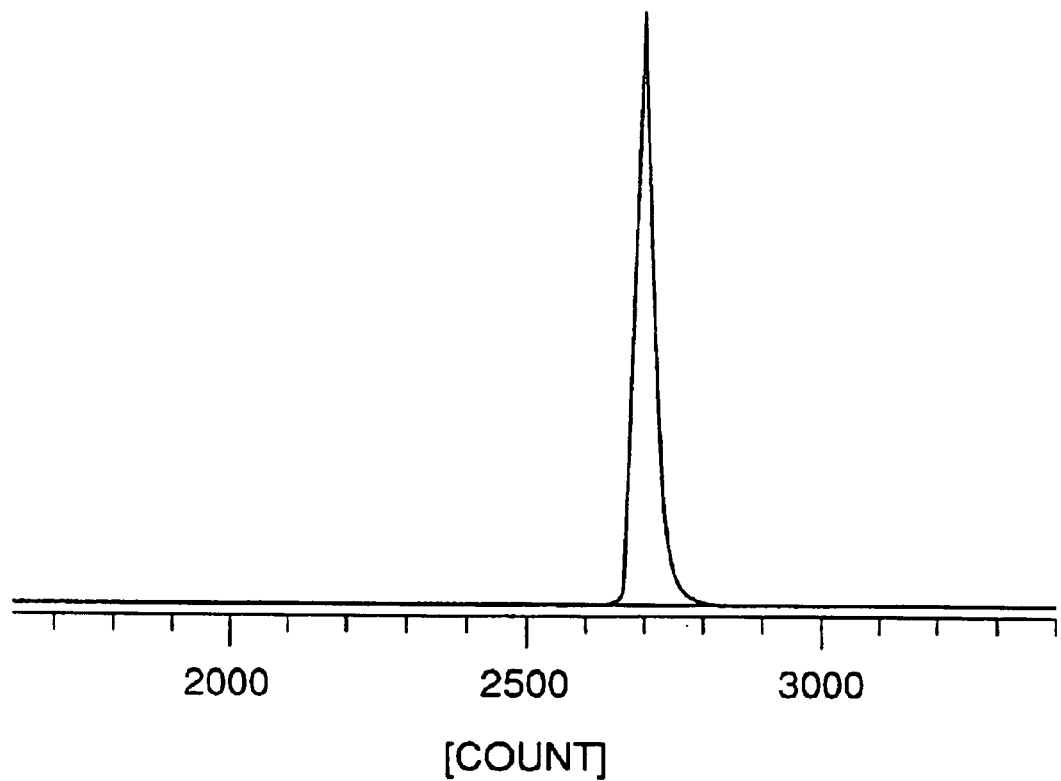
FIG. 1 is the GPC chart of a hydroxy compound.
Figure 2:
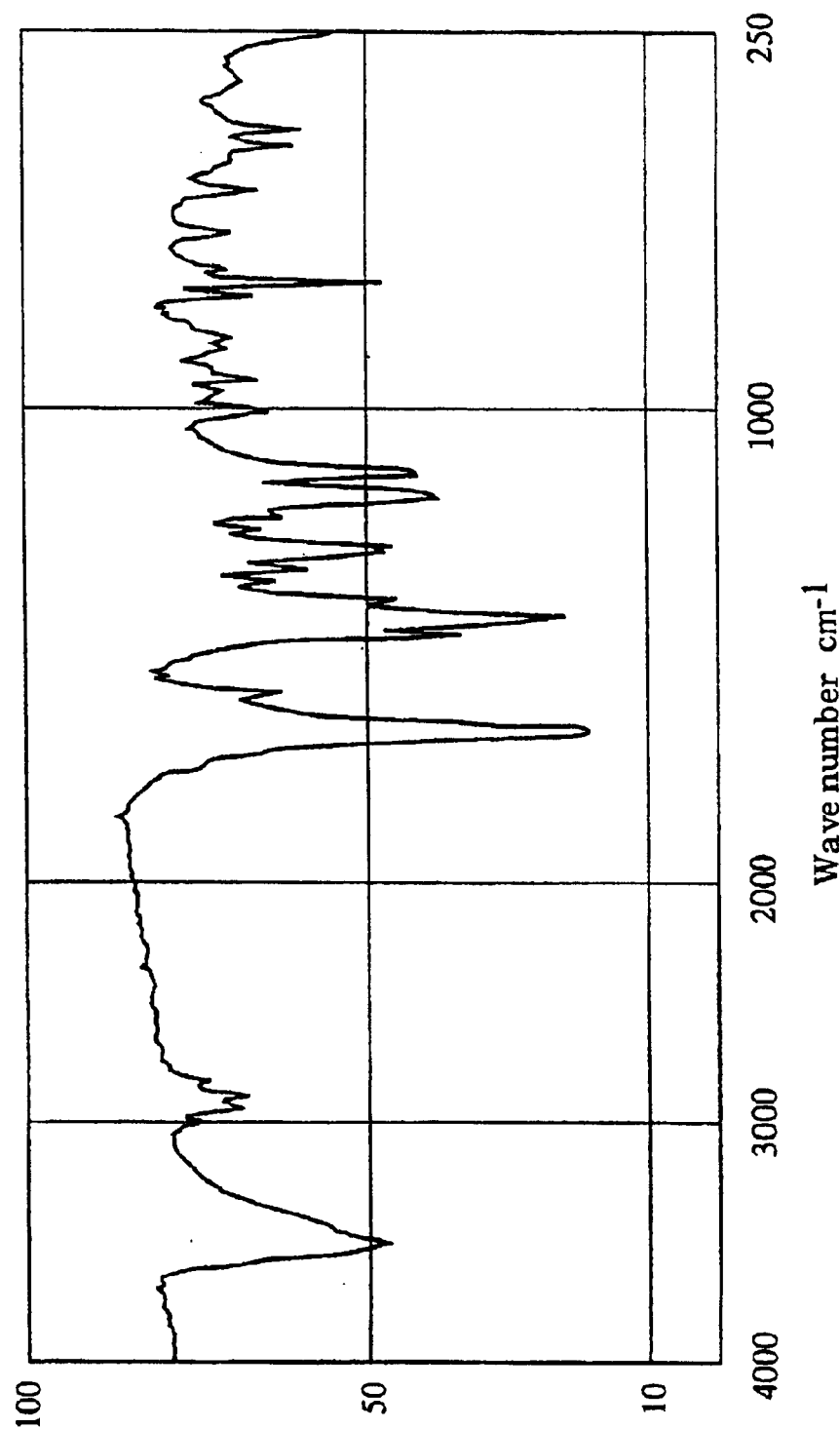
FIG. 2 is the IR absorption spectrum of said hydroxy compound.

The GPC chart of the hydroxy compound is shown in FIG. 1 and the infrared absorption spectrum in FIG. 2. The data read off the FD-MS chart and the analysis of H-NMR spectrometry conducted in acetone-d6 are given below.

FD-MS (m/z: peak intensity) 226:9.5, 398:9.8, 532:100
H-NMR [δ (ppm): signal pattern: assignment] 2.16: s, 18H: methyl proton; 4.87: s, 6H: benzyl proton; 6.99: s, 6H: aromatic proton; 7.21: s, 3H; hydroxyl proton The GPC measurements were made under the following conditions: apparatus, HLC-82A (available from Tosoh Corporation); columns, TSK-GEL 2000×3 and TSK-GEL 4000×1 (available from Tosoh Corporation); solvent, tetrahydrofuran; flow rate, 1.0 ml/min; temperature 38° C.; detector, RI.

The principal component of the product is Compound 1 which is the reaction product obtained at the cyanuric acid to 2,6-xylenol ratio of 1:3. Although the FD-MS measurement confirmed the formation of Compound 2 (m/z=398) which is the reaction product obtained at the cyanuric acid to 2,6-xylenol ratio of 1:2 and Compound 3 (m/z=266)

which is the reaction product obtained at the cyanuric acid to 2,6-xylenol ratio of 1:1 as byproducts, the GPC measurement indicated the formation of 98% or more of Compound 1 and 2% or less of Compounds 2 and 3.

EXAMPLE 1

Synthesis of Epoxy Resin

In 700 g of epichlorohydrin was dissolved 100 g of the hydroxy compound obtained in Synthesis Example 1 and to the resulting solution was added 37.5 g of a 48% aqueous solution of sodium hydroxide in drops at 70° C. under a reduced pressure (approximately 150 mmHg) over a period of 3.5 hours. During this period, the water formed was taken out of the system together with a part of the epichlorohydrin by azeotropic distillation and the distilled epichlorohydrin was returned to the system. Upon completion of the addition in drops of the aqueous sodium hydroxide, the reaction was continued for another 30 minutes. Thereafter, the salt formed was filtered off, the reaction mixture was washed further with water and stripped of the epichlorohydrin by distillation to give 124 g of an epoxy resin with a softening point of 81° C., a melt viscosity at 150° C. of 0.6 Pa·s and an epoxy equivalent of 282 g/eq.

Figure 3:
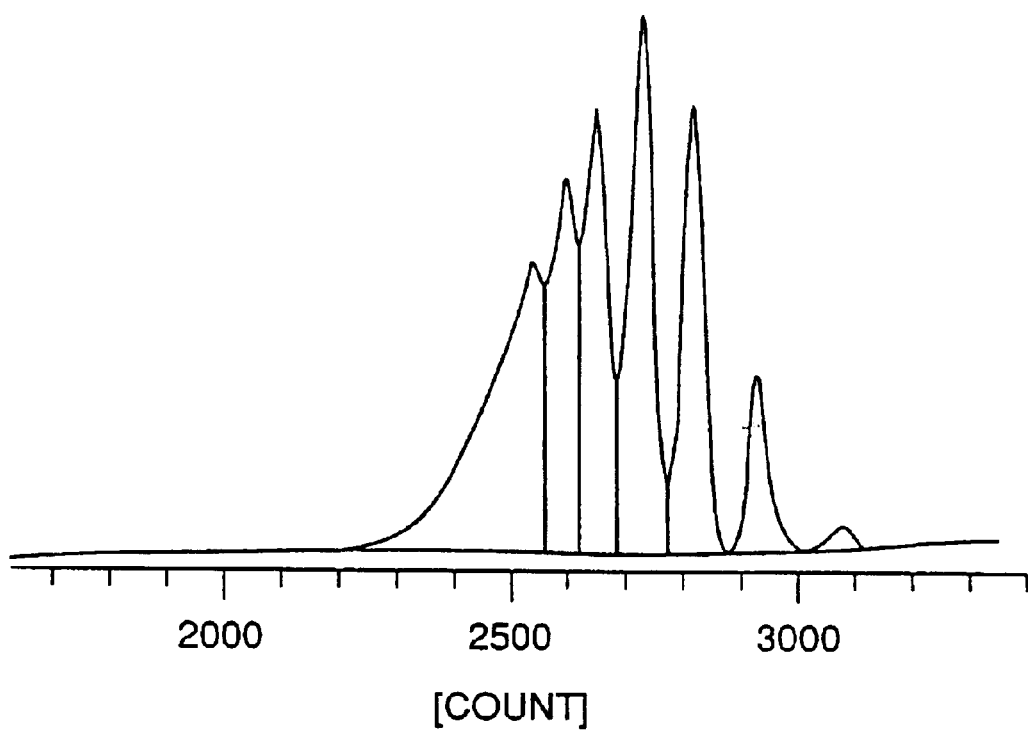
FIG. 3 is the GPC chart of an epoxy resin of this invention.
Figure 4:
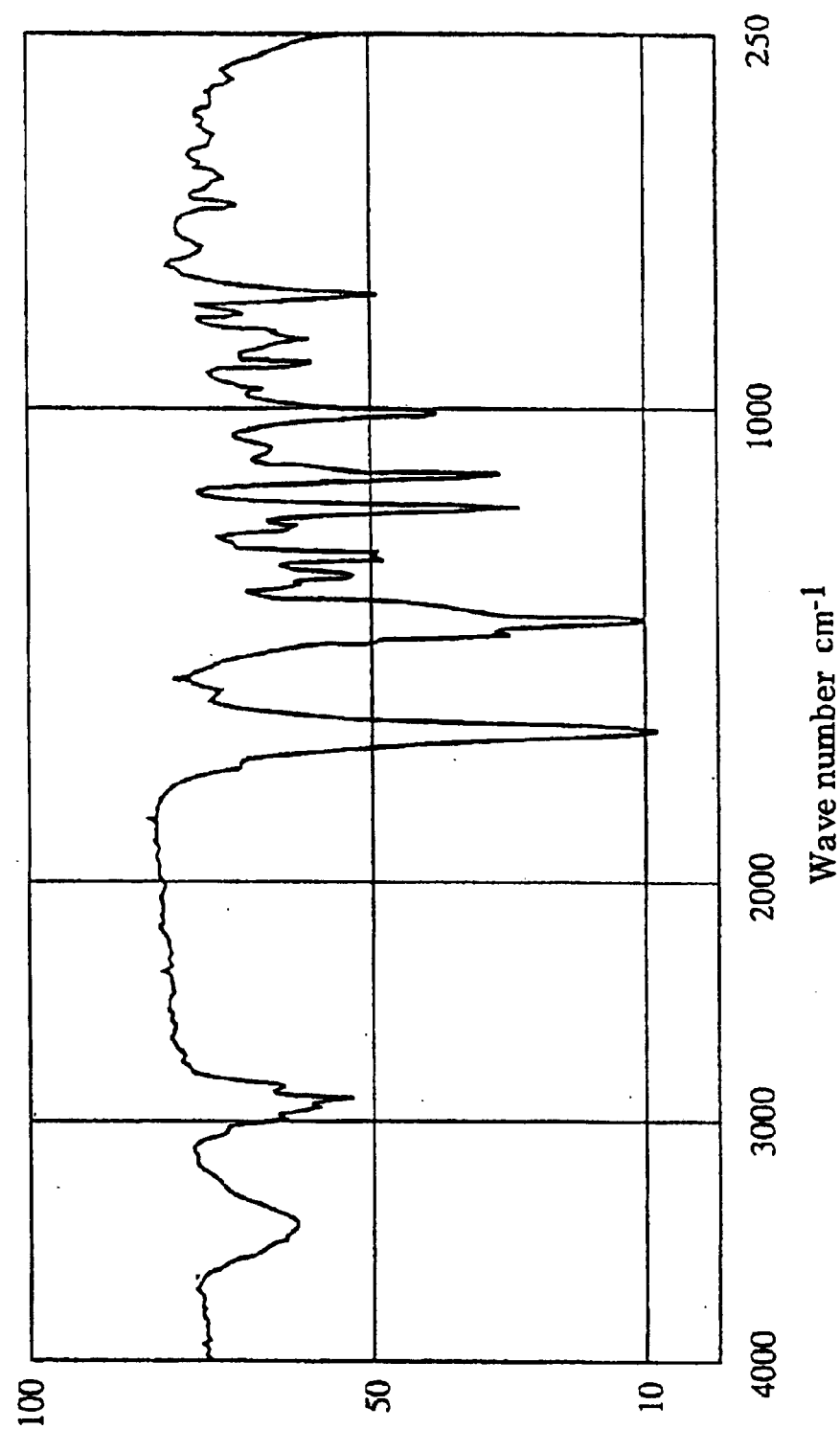
FIG. 4 is the IR absorption spectrum of said epoxy resin.

The GPC chart of the epoxy resin thus obtained is shown in FIG. 3 and the infrared absorption spectrum in FIG. 4. The data read off the FD-MS chart and the analysis of H-NMR spectrometry conducted in acetone-d6 are given below.

FD-MS (m/z: peak intensity) 57:10.2, 135:9.8, 191:100, 283:30.5, 331:7.9, 369:25.2, 398:8.5, 432:38.8, 464:14.1, 566:73.5, 659:7.5, 700:83.6, 793:15.2 H-NMR [δ (ppm): signal pattern: assignment] 2.21–2.30: m, 18H: methyl proton; 2.58–2.81: m, 6H: methylene proton; 3.15–3.31: m, 3H: methine proton; 3.59–4.14: m, 6H: methylene proton; 4.63–4.94: m, 6H: benzyl proton; 7.04–7.18: m, 6H: aromatic proton The FD-MS measurement confirmed the formation of epoxidized Compound 1 (m/z=700), epoxidized Compound 2 (m/z=566) and epoxidized Compound 3 (m/z=432). The GPC measurement indicated the formation of 22% of epoxidized Compound 1, 15% of epoxidized Compound 2, 6% of epoxidized Compound 3 and 57% of dimers and polymers.

SYNTHESIS EXAMPLE 2

Synthesis of Hydroxy Compound

In a 2-L four-necked flask were placed 67.7 g of cyanuric acid, 600 g of phenol, 62.0 g of 92% paraformaldehyde, 0.9 g of hexamethylenetetramine, 580 mL of dimethylformamide and 15 mL of pure water and the mixture was allowed to react with stirring under reflux at approximately 116° C. for 20 hours in a stream of nitrogen. After the reaction was over, the reaction mixture was stripped of the dimethylformamide and the unreacted phenol by distillation under reduced pressure at 200° C. to give 202 g of a brown hydroxy compound with a hydroxyl equivalent of 171 g/eq. and a softening point of 145° C. The data read off the FD-MS chart are as follows.

FD-MS (m/z: peak intensity) 71:26, 107:41, 150:60, 200:28, 235:26, 311:31, 341:38, 447:100, 553:73, 589:14, 766:8

The FD-MS measurement confirmed the formation of Compound 4 (m/z=235) which is the reaction product at the cyanuric acid to phenol ratio of 1:1, Compound 5 (m/z=341) which is the reaction product at the cyanuric acid to phenol ratio of 1:2 and Compound 6 (m/z=447) which is the reaction product at the cyanuric acid to phenol ratio of 1:3 and, in addition, Compound 7 (m/z=553) which is the reaction product at the cyanuric acid to phenol ratio of 1:4.

EXAMPLE 2

Synthesis of Epoxy Resin

In 1,100 g of epichlorohydrin and 200 g of diglyme was dissolved 100 g of the hydroxy compound obtained in Synthesis Example 2 and to the resulting solution was added 50.2 g of a 48% aqueous solution of sodium hydroxide in drops at 70° C. under a reduced pressure (approximately 80 mmHg) over a period of 3.5 hours. During this period, the water formed was taken out of the system together with a part of the epichlorohydrin by azeotropic distillation and the distilled epichlorohydrin was returned to the system. Upon completion of the addition in drops of the aqueous sodium hydroxide, the reaction was continued for another 30 minutes. Thereafter, the reaction mixture was stripped of the epichlorohydrin by distillation, dissolved in 660 g of methyl isobutyl ketone, separated from the salt formed by filtration, washed further with water and stripped of the methyl isobutyl ketone by distillation to give 108 g of an epoxy resin with a softening point of 131° C., a melt viscosity at 150° C. of 0.95 Pa·s and an epoxy equivalent of 253 g/eq.

EXAMPLES 3–7 AND COMPARATIVE EXAMPLES 1–2

Epoxy resin compositions were formulated as shown in Table 1 by the use of the epoxy resins synthesized in Examples 1 and 2, o-cresol novolak type epoxy resin (Epoxy resin A; EOCN-1020-65 with an epoxy equivalent of 200, a hydrolyzable chlorine content of 400 ppm and a softening point of 65° C., available from Nippon Kayaku Co., Ltd.) and biphenyl type epoxy resin (Epoxy resin B; YX4000HK with an epoxy equivalent of 195, a hydrolyzable chlorine content of 450 ppm and a softening point of 105° C., available from Yuka Shell Epoxy K.K.) as epoxy resin and the hydroxy compound synthesized in Synthesis Example 1, phenol novolak (Curing agent A; PSM-4261 with a hydroxyl equivalent of 103 and a softening point of 80° C., available from Gun-ei Chemical Industry Co., Ltd.) and naphthol aralkyl type resin (Curing agent B; SN-475 with a hydroxyl equivalent of 210 and a softening point of 77° C., available from Nippon Steel Chemical Co., Ltd.) as a curing agent. In addition, spherical silica (average particle diameter, 18 μm) was used as a filler and triphenylphosphine as a curing accelerator.

In Table 1, Epoxy resin 1 is the epoxy resin obtained in Example 1, Epoxy resin 2 is the epoxy resin obtained in Example 2 and the Hydroxy compound 1 is the hydroxy compound obtained in Synthesis Example 1.

The numerical values in the table denote parts by weight.

TABLE 1

|  | Ex. 3 | Ex. 4 | Ex. 5 | Ex. 6 | Ex. 7 | Comp. Ex. 1 | Comp. Ex. 2 |
|---|---|---|---|---|---|---|---|
| Epoxy resin 1 | 110 | 94 | 39 | 90 |  |  |  |
| Epoxy resin 2 |  |  |  |  | 107 |  |  |
| Epoxy resin A |  |  |  |  |  | 99 |  |
| Epoxy resin B |  |  | 39 |  |  |  | 72 |
| Hydroxy compound 1 |  |  |  | 20 |  |  |  |
| Curing agent A | 40 |  |  |  | 43 | 51 |  |
| Curing agent B |  | 56 | 72 | 40 |  |  | 78 |

TABLE 1-continued

| | Ex. 3 | Ex. 4 | Ex. 5 | Ex. 6 | Ex. 7 | Comp. Ex. 1 | Comp. Ex. 2 |
|---|---|---|---|---|---|---|---|
| Spherical silica | 800 | 800 | 800 | 800 | 450 | 800 | 800 |
| Curing accelerator | 2.1 | 2.1 | 2.1 | 2.1 | 2.1 | 1.2 | 1.2 |
| Carbon black | 5 | 5 | 5 | 5 | 5 | 5 | 5 |
| Carnauba wax | 3 | 3 | 3 | 3 | 3 | 3 | 3 |
| Silica content (wt %) | 83 | 83 | 83 | 83 | 74 | 83 | 83 |

The epoxy resin compositions were molded at 175° C., then postcured at 180° C. for 12 hours and the cured specimens were tested for a variety of properties. The results are shown in Table 2.

The glass transition temperature and linear expansion coefficient were determined by the use of a thermomechanical analyzer at a rate of temperature rise of 10° C./min. The water absorption was determined by leaving a circular specimen, 50 mm in diameter and 3 mm in thickness, under the conditions of 85° C. and 85% RH for 100 hours and measuring the change in weight. The burning time was determined on 1/16 inch-thick specimens in accordance with UL94V-0 and expressed as the total burning time of five test specimens. The adhesive strength was evaluated by placing a molded article, 25 mm×12.5 mm×0.5 mm, between two copper sheets, molding at 175° C. in a compression molding machine, postcuring at 180° C. for 12 hours, and determining the tensile shear strength.

TABLE 2

| | Ex. 3 | Ex. 4 | Ex. 5 | Ex. 6 | Ex. 7 | Comp. Ex. 1 | Comp. Ex. 2 |
|---|---|---|---|---|---|---|---|
| Burning time (sec) | 76 | 32 | 88 | 14 | 25 | >300*[1] | 235 |
| Spiral flow (cm) | 78.0 | 68.5 | 82.0 | 56.0 | 57.0 | 85.0 | 98.5 |
| Gel time (sec) | 30 | 25 | 27 | 21 | 28 | 31 | 30 |
| Hardness at elevated temperature | 72 | 67 | 68 | 54 | 78 | 77 | 62 |
| Thermal expansion coefficient (<Tg, × $10^{-5}$) | 1.0 | 1.0 | 1.0 | 1.0 | 1.5 | 1.1 | 1.0 |
| Thermal expansion coefficient (>Tg, × $10^{-5}$) | 3.9 | 3.8 | 3.7 | 3.7 | 5.7 | 4.2 | 4.0 |
| Glass transition temperature (° C.) | 174 | 134 | 154 | 141 | 181 | 163 | 124 |
| Flexural strength (MPa) | 180 | 184 | 188 | 172 | 178 | 174 | 171 |
| Flexural modulus (GPa) | 22.2 | 22.3 | 22.0 | 22.5 | 18.1 | 21.3 | 21.0 |
| Water absorption (wt %, 100 h) | 0.21 | 0.17 | 0.16 | 0.23 | 0.20 | 0.23 | 0.19 |
| Adhesive strength (MPa,Cu) | 2.1 | 2.4 | 2.8 | 2.2 | 2.2 | 1.2 | 1.6 |

*[1]In all the specimens tested, the flame reached the upper end of the test specimen without self extinguishing.

INDUSTRIAL APPLICABILITY

The cured articles obtained by curing epoxy resin compositions comprising the epoxy resins of this invention have excellent properties in respect to flame retardance, adhesiveness, moisture resistance and heat resistance and can be used in applications such as lamination, molding, casting and adhesion.

What is claimed is:
1. Epoxy resins represented by the following general formula (3);

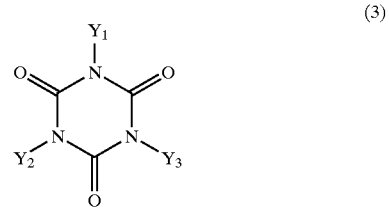

(3)

wherein $Y_1$ denotes a glycidyloxyarylmethyl group represented by the following general formula (4)

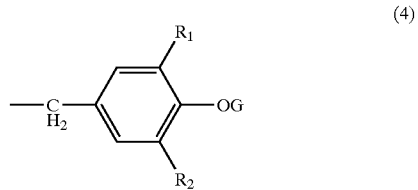

(4)

(wherein $R_1$ and $R_2$ denote independently a hydrogen atom or a hydrocarbon group containing 1 to 8 carbon atoms and G denotes a glycidyl group) and $Y_2$ and $Y_3$ denote independently a glycidyl group or the aforementioned glycidyloxyarylmethyl group.

2. An epoxy resin compositions comprising epoxy resins and curing agents, wherein said epoxy resins comprise the epoxy resins of claim 1 as essential components.

3. Cured articles obtained by curing the epoxy resin compositions described in claim 2.

4. A process for preparing epoxy resins which comprises allowing a hydroxy compound represented by the following general formula (1) to react with epichlorohydrin;

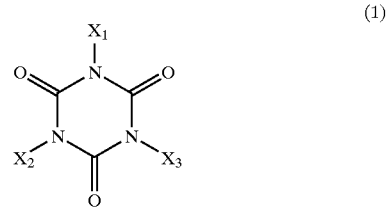

(1)

wherein $X_1$ denotes a hydroxyarylmethyl group represented by the following general formula (2)

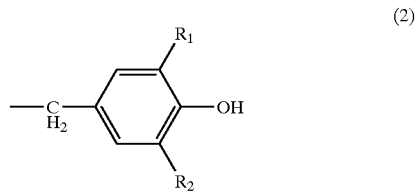

(2)

wherein $R_1$ and $R_2$ denote independently a hydrogen atom or a hydrocarbon group containing 1 to 8 carbon atoms) and $X_2$ and $X_3$ denote independently a hydrogen atom or said hydroxyarylmethyl group.

* * * * *